(12) United States Patent
Deligianni et al.

(10) Patent No.: US 11,311,233 B2
(45) Date of Patent: Apr. 26, 2022

(54) INTELLIGENT AND DISPOSABLE DEVICE FOR SELECTIVE ELECTRICAL STIMULATION OF APOPTOSIS

(71) Applicant: INTERNATIONAL BUSINESS MACHINES CORPORATION, Armonk, NY (US)

(72) Inventors: Hariklia Deligianni, Yorktown Heights, NY (US); Bruce B. Doris, Slingerlands, NY (US); Steven J. Holmes, Yorktown Heights, NY (US); Emily R. Kinser, Poughkeepsie, NY (US); Qinghuang Lin, Yorktown Heights, NY (US); Roy R. Yu, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 595 days.

(21) Appl. No.: 15/602,343

(22) Filed: May 23, 2017

(65) Prior Publication Data

US 2018/0339154 A1    Nov. 29, 2018

(51) Int. Cl.
| | | |
|---|---|---|
| A61B 5/00 | (2006.01) | |
| A61B 5/145 | (2006.01) | |
| A61B 5/06 | (2006.01) | |
| H01L 23/58 | (2006.01) | |

(52) U.S. Cl.
CPC ........ *A61B 5/4836* (2013.01); *A61B 5/14539* (2013.01); *H01L 23/58* (2013.01); *A61B 5/062* (2013.01); *A61B 5/686* (2013.01); *A61B 5/6852* (2013.01); *A61B 2562/0285* (2013.01); *A61B 2562/125* (2013.01)

(58) Field of Classification Search
CPC ........ A61N 1/36; A61B 5/062; A61B 5/4836; A61B 5/14539
See application file for complete search history.

(56) References Cited

U.S. PATENT DOCUMENTS

| | | | | |
|---|---|---|---|---|
| 6,733,485 B1 * | 5/2004 | Whitehurst | ......... | A61M 31/002 604/20 |
| 8,781,576 B2 * | 7/2014 | Savage | .................... | A61N 1/39 607/5 |
| 2010/0240995 A1 * | 9/2010 | Nuccitelli | .......... | A61B 18/1492 600/439 |

(Continued)

OTHER PUBLICATIONS

Beebe, S.J. et al., "Nanosecond Pulsed Electric Field (nsPEF) Effects on Cells and Tissues: Apoptosis Induction and Tumor Growth Inhibition" IEEE Transactions on Plasma Science (Feb. 2002) pp. 286-292, vol. 30, No. 1.

(Continued)

*Primary Examiner* — William J Levicky
(74) *Attorney, Agent, or Firm* — Tutunjian & Bitetto, P.C.; L. Jeffrey Kelly

(57) ABSTRACT

A sensing and treatment device includes an array of metal nanorod electrodes formed on a substrate, the array including first electrodes for sensing, and second electrodes for electrical pulsation. A data processing system is configured to monitor a parameter using the first electrodes and to activate the electrical pulsation in the second electrodes in accordance with a reading of the parameter.

12 Claims, 9 Drawing Sheets

(56) References Cited

U.S. PATENT DOCUMENTS

| | | | | |
|---|---|---|---|---|
| 2011/0028803 A1* | 2/2011 | Ollmar | ............... | A61B 5/0531 |
| | | | | 600/301 |
| 2011/0054583 A1* | 3/2011 | Litt | ................ | A61B 5/0031 |
| | | | | 607/116 |
| 2011/0184690 A1* | 7/2011 | Iida | ................ | A61B 1/00158 |
| | | | | 702/150 |
| 2014/0358066 A1* | 12/2014 | Nuccitelli | ............... | A61N 1/36 |
| | | | | 604/20 |

OTHER PUBLICATIONS

Choudhary, N. et al., "High-Performance One-Body Core/Shell Nanowire Supercapacitor Enabled by Conformal Growth of Capacitive 2D WS2 Layers" ACS Nano (Oct. 2016) pp. 10726-10735, vol. 10, No. 13.

Gerweck, L.E. et al., "Cellular pH Gradient in Tumor versus Normal Tissue: Potential Exploitation for the Treatment of Cancer" Cancer Research (Mar. 1996) pp. 1194-1198, vol. 56.

Zhang, X. et al., "Tumor pH and its measurement" Journal of Nucl. Med. (Aug. 2010) pp. 1167-1170, vol. 51, No. 8.

U.S. Office Action issued in related U.S. Appl. No. 15/808,137, dated May 4, 2018, pp. 1-24.

* cited by examiner

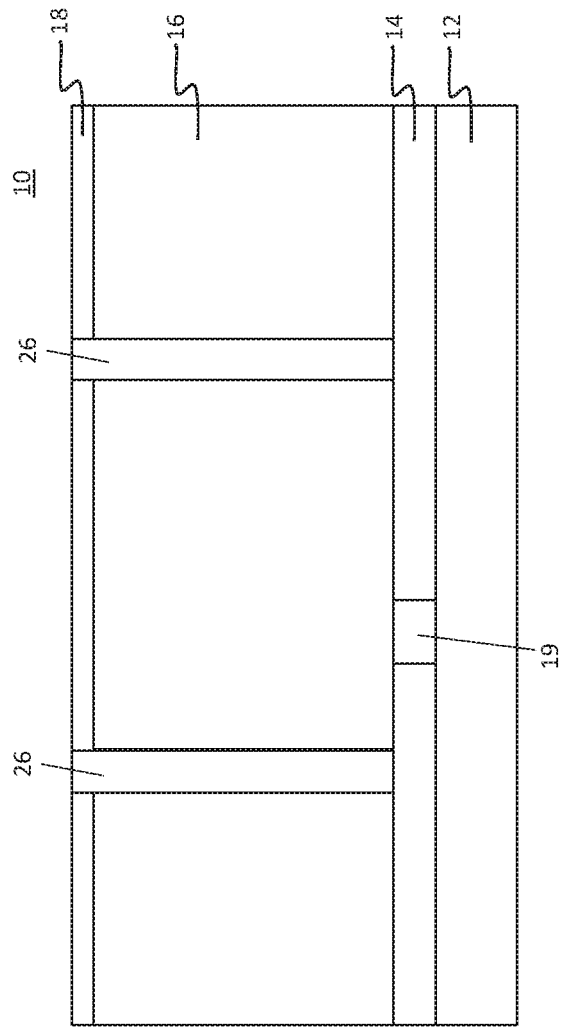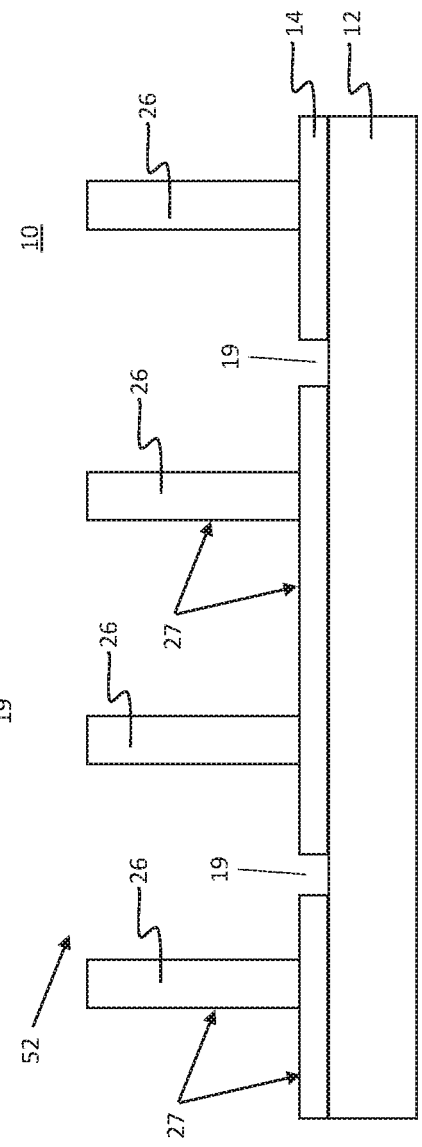

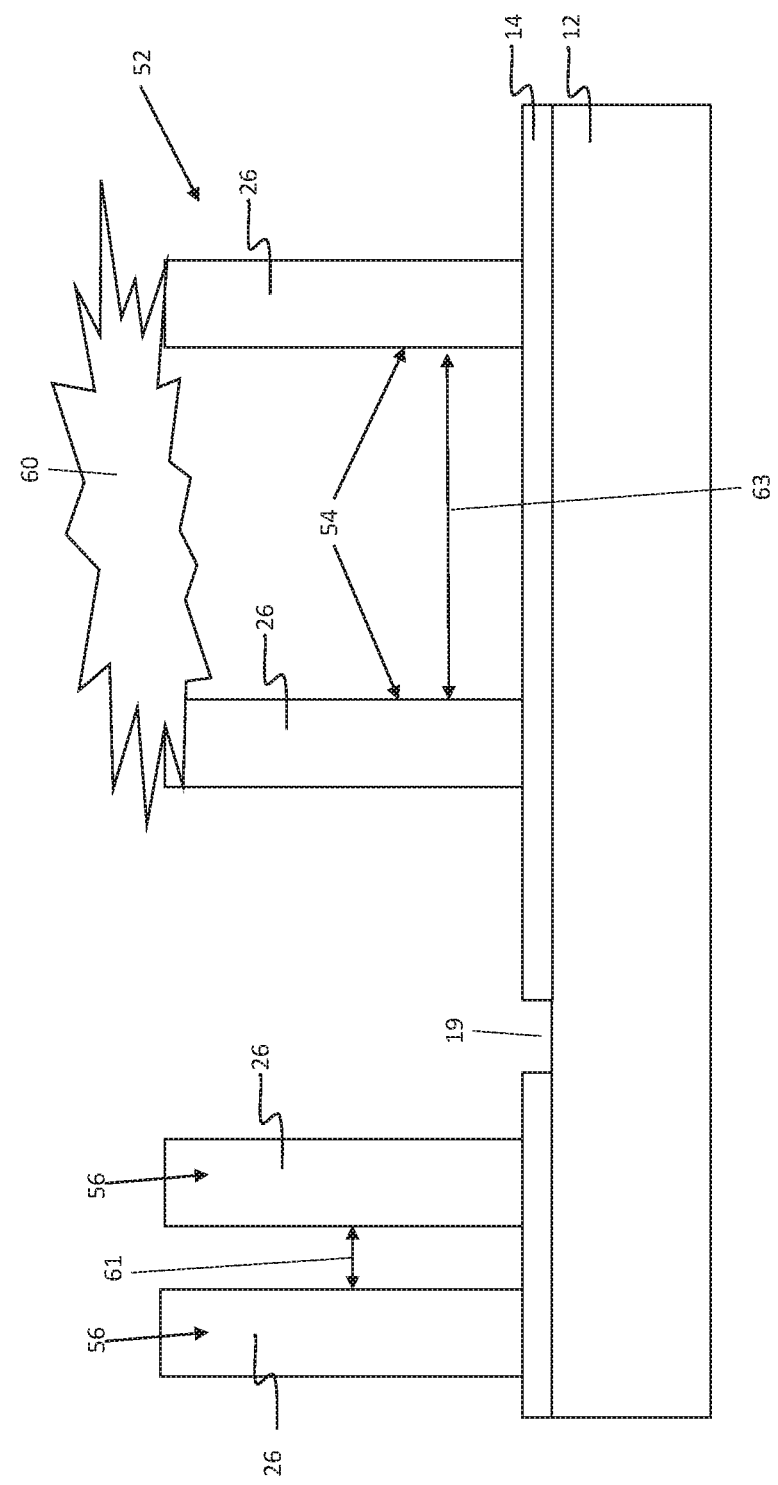

INTELLIGENT AND DISPOSABLE DEVICE FOR SELECTIVE ELECTRICAL STIMULATION OF APOPTOSIS

BACKGROUND

Technical Field

The present invention generally relates to biosensing and stimulation devices, and more particularly to implantable devices and methods for selective electrical stimulation for apoptosis.

Description of the Related Art

Electrical stimulation of apoptosis has been identified as an effective treatment of some types of cancer, using macroscopic non-intelligent electrodes (e.g., tumor ablation systems). Localized tumors have been treated in this way, to both induce cellular death and also to stimulate the immune system to recognize and destroy cancer cells. Some types of cancer are more diffuse and difficult to target with a macroscopic electrode, and some parts of the body, such as brain tissue, are more difficult to access with a macroscopic electrode. In addition, some parts of the body, such as tissue in the brain, blood, lymph, urinary system, etc. are also difficult to access with a macroscopic electrode.

SUMMARY

In accordance with an embodiment of the present invention, a sensing and treatment device includes an array of metal nanorod electrodes formed on a substrate, the array including first electrodes for sensing, and second electrodes for electrical pulsation. A data processing system is configured to monitor a parameter using the first electrodes and to activate the electrical pulsation in the second electrodes in accordance with a reading of the parameter.

Another embodiment includes a sensing and treatment device having an array of metal nanorod electrodes formed on a substrate. The array includes first electrodes for pH sensing, and second electrodes for electrical pulsation. A data processing system is configured to monitor pH using the first electrodes and to activate the electrical pulsation in the second electrodes in accordance with a pH reading.

Another sensing and treatment device includes a flexible elongated instrument configured for deployment in vivo and an array of metal nanorod electrodes formed on a substrate and mounted on a proximal end portion of the flexible elongated instrument. The array includes first electrodes for pH sensing, and second electrodes for electrical pulsation. A data processing system is configured to monitor pH using the first electrodes and to activate the electrical pulsation in the second electrodes in accordance with a pH reading.

A method for fabricating a medical device includes patterning a metal layer on a substrate; forming nanorods on the metal layer; connecting first portions of the nanorods to an integrated data processing system to function as sensor electrodes; and connecting second portions of the nanorods to the integrated data processing system to function as electrical pulsing electrodes.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 5 is a cross-sectional view showing the substrate of FIG. 4 having nanorods plated and connecting to the metal layer and planarized to the hard mask layer for forming nanorods in accordance with an embodiment of the present invention;

FIG. 6 is a cross-sectional view showing nanorods formed on the patterned metal layer in accordance with an embodiment of the present invention;

FIG. 7 is a cross-sectional view showing the device of FIG. 6 being deployed in vivo with cells interacting with the device in accordance with an embodiment of the present invention;

DETAILED DESCRIPTION

Figure 1:
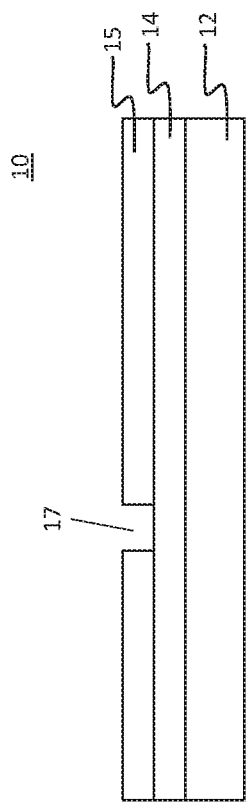
FIG. 1 is a cross-sectional view showing a substrate having a metal layer and a patterned resist formed thereon for forming nanorods in accordance with an embodiment of the present invention.

In accordance with embodiments of the present invention, medical devices and methods for fabrication of these devices are provided. The devices can incorporate a combination of active sensors, nano-pulse regions and regions of energy storage. The devices can include a control mechanism to activate electrical nano-pulses when appropriate cellular conditions are sensed. Processes for making these devices or sensors can include integration on or with a semiconductor chip. These devices can be employed for treating specific diseases. In one embodiment, the device or devices can be deployed laparoscopically as part of a medical instrument or the device can be introduced and controlled externally. The medical instrument can include several elements and perform multiple functions.

In one useful embodiment, an array of sensor elements on the device can be employed to detect cancer cells by measuring pH, for example. The array is composed of nanorods arranged in a blocks, e.g., in a range of array sizes, e.g., squares with sides in the range of about 1 micron to 100 microns, preferably about 5-10 microns. Other shapes and sized arrays are also contemplated. Adjacent to each block of nanorods is another block of nanorods capable of delivering significant voltage to kill only the cancer cells. Alternatively, the array is composed of interspersed probes that alternately sense pH with every other probe or so having a capability to deliver voltage to kill cells. Groups of probes can be isolated electrically from each other.

The devices can include their own integrated microprocessor or computer with an algorithm programmed to identify cells, e.g., cancer cells, from the pH measured by the array, and program a pulse of voltage to the cells. This is an intelligent component of device, others are possible as well. Memory on the device can be employed to store data regarding positions of cells, e.g., cancer cells or healthy cells relative to the cancer cells.

In one embodiment, the device can be employed as a 'nano-bot' that has a set of nano-electrodes that function both as a pH sensor and a voltage nano-pulse array. The device can be permitted to circulate in biological systems, e.g., blood or urinary tract or within an organ. When undesired biological systems are detected, such as cancerous tissue, via pH deviations, a high voltage nano-pulse sequence is activated through the nano-rods to induce apoptosis of tissue in proximity to the device.

The microprocessor can be incorporated into the nano-rod array, and use the nano-rod array both as a sensor device to sense regions of cancer cell growth, and also to selectively activate portions of the array to direct nano-pulses of electrical voltage at the specific location of the cancer cells to induce apoptosis. The location of the treatment can be moved and adjusted by the use of magnetic fields external to a patient. In this way, destruction of healthy tissue can be avoided in the body while effectively treating a diffuse cancer growth. All types of diffuse cancer could also be treated in this way, e.g., pancreatic, liver or lymphoma cancer. A medical instrument with integral sensor arrays can also be employed to detect cancer and deliver local voltage pulses to kill selected cancer cells. The medical instrument can include, e.g., a catheter or guide wire, that can pinpoint the location of cancer cells and apply voltage to kill selected cells.

In useful embodiments, a substrate having electronics or connections to electronics can include one or more nanorods. The nanorods can include inert metals, such as Pt or the like. The nanorods are vertically disposed and have a diameter or transverse width of between about 20 nm to about 3 microns, preferably between about 100 nm to about 500 nm, although other useful sizes are contemplated. The nanorods can be arranged in an array or other configuration on the substrate to promote collection of materials or enhance the presence of materials. Combinations of the features described can also be employed together.

A dielectric layer can be formed on the metallic nanorods or pillars, to provide insulation from the biological environment, Such dielectric can be formed by, e.g., atomic layer deposition.

It is to be understood that aspects of the present invention will be described in terms of a given illustrative architecture; however, other architectures, structures, substrate materials and process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGs. It will be understood that the spatially relative terms are intended to encompass different orientations of the device in use or operation in addition to the orientation depicted in the FIGs. For example, if the device in the FIGs. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, a partially fabricated biosensor device 10 is shown in accordance with one embodiment. The device 10 includes a substrate 12 having one or more layers formed thereon. The substrate 12 can include any suitable substrate structure, e.g., a bulk semiconductor, a semiconductor-on-insulator (SOI) substrate, etc. In one example, the substrate 12 can include a silicon-containing material. Illustrative examples of Si-containing materials suitable for the substrate 12 can include, but are not limited to, Si, SiGe, SiGeC, SiC and multi-layers thereof. Although silicon is the predominantly used semiconductor material in wafer fabrication, alternative semiconductor materials can be employed as additional layers, such as, but not limited to, germanium, gallium arsenide, gallium nitride, silicon germanium, cadmium telluride, zinc selenide, etc.

Since the present embodiments provide a device that can work remotely, the device 10 can include a substrate have powered circuitry for controlling the functions of the device 10. In this way, the substrate 12 can include control circuitry fabricated using known semiconductor processing techniques. Components can include transistors, metal lines, capacitors, logic gates or any other electronic components that permit the control of the nanorods and other structures to be formed in subsequent steps. In one useful embodiment, bipolar junction transistors (BJT) can be employed in the circuitry formed in the substrate 12. BJT devices can be employed to generate sub-nanosecond pulsing, as will be described.

A metal layer 14 is deposited on the substrate 12. The metal layer 14 can include a conductive but relatively inert metal, such as, e.g., Pt, Au, Ag, Cu, Jr, Ru, Rh, Re, Os, Pd, and their oxides (e.g., $IrO_2$, RuOx, etc.), although other metals, metal oxides and their alloys can be employed. The metal layer 14 can be formed by deposition using a sputtering process, chemical vapor deposition (CVD) process, atomic layer deposition (ALD), a plating process or any other suitable deposition process.

A resist layer 15 is formed on the metal layer 15. The resist layer 15 can be spun on. The resist layer 15 is patterned to form openings 17 that will be employed to pattern electrode bases to connect groups of nanorods, which be formed in later steps.

Figure 2:
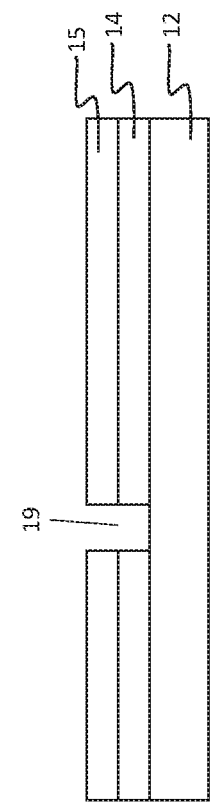
FIG. 2 is a cross-sectional view showing the substrate of FIG. 1 having the metal layer patterned in accordance with an embodiment of the present invention.

Referring to FIG. 2, a wet etch or dry etch, e.g., reactive ion etch (RIE) can be performed to pattern the metal layer 14 to form openings 19 down to the substrate 12. The pattern can include sufficient detail to connect any nanorods to be formed (e.g., groups of two or more in any combination). The resist layer 15 is then removed. The patterned metal layer 14 can also include metal lines and connections to circuits or chips, as needed.

Figure 3:
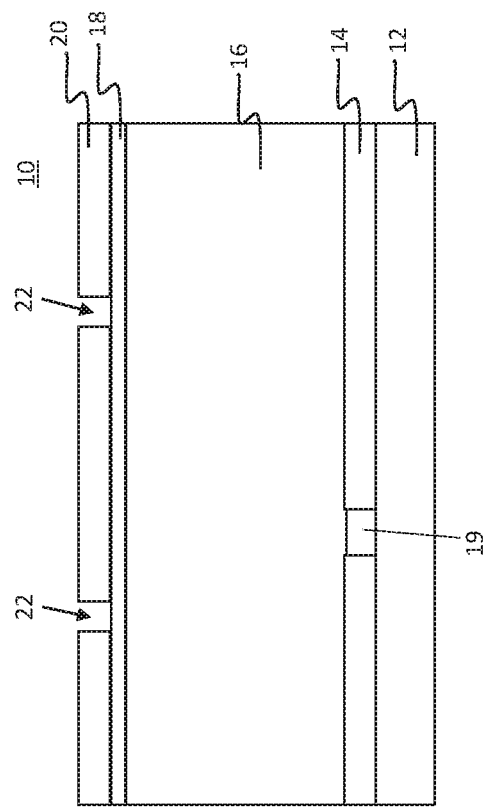
FIG. 3 is a cross-sectional view showing the substrate of FIG. 2 having an organic planarizing layer, hard mask layer and patterned resist formed thereon for forming nanorods in accordance with an embodiment of the present invention.

Referring to FIG. 3, in one embodiment, an organic planarizing layer (OPL) 16 is formed on the patterned metal layer 14. The OPL 16 can be formed by a spin-on process or other deposition process. In useful embodiments, the OPL 16 can be formed on a layer to assist in the removal of the OPL 16.

An etch stop layer or hard mask 18 can be deposited over the OPL 16. In one embodiment the etch stop layer 18 can include a metal, such as, e.g., Ti, Ta, etc. or a metallic compound such as, e.g., TiN, TaN, SiARC (a silicon containing organic ARC layer), TiARC (a titanium ARC), etc. Another resist layer 20 is formed on the etch stop layer or hard mask 18. The resist layer 20 can be spun on. The resist layer 20 is patterned to form openings 22 that will be employed to form nanorods, as will be described.

Figure 4:
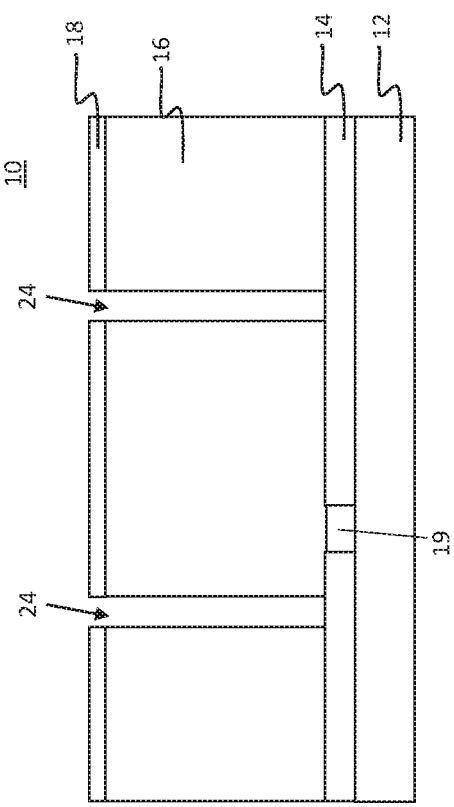
FIG. 4 is a cross-sectional view showing the substrate of FIG. 3 having the metal layer exposed by etching the organic planarizing layer in accordance with the hard mask layer and the patterned resist for forming nanorods in accordance with an embodiment of the present invention.

Referring to FIG. 4, an etch process is performed to open up the etch stop layer 18. In one embodiment, a reactive ion etch (RIE) process can be performed to expose the OPL 16 through the openings 22 (FIG. 1). Then, a reactive ion etch (RIE) is performed to etch through the OPL 16 to expose the metal layer 14 and form trenches 24 in accordance with the resist 20 and/or the etch stop layer or hard mask 18. The trenches 24 provide locations for the formation of nanorods. The etch of OPL 16 should be minimized to maintain small critical dimensions (CDs) for the hole or trench 24 to be plated.

Referring to FIG. 5, a metal deposition process is performed and can include a plating process, chemical vapor deposition (CVD), ALD or the like. The metal of the deposition process preferably includes a same metal as employed in metal layer 14. In one particularly useful embodiment, the metal of layer 14 and the metal used in nanorods 26 can include Pt, Ag, Au, Cu, Jr, Ru, Rh, Re, Os, Pd, and their oxides (e.g., $IrO_2$, RuOx, etc.), although other metals, metal oxides, conductive materials and their alloys can be employed. The nanorods 26 can be annealed with the OPL 16 present or with the OPL 16 removed. If the hard mask 18 includes, e.g., Ti or TiN, the hard mask 18 can be removed with hydrogen peroxide aqueous solution, or if it is Ti oxide or TiARC, it can be removed with diluted HF, as wet etching is simpler and easier to control than planarization processes such as, e.g., a chemical mechanical polish (CMP). However, a planarization process, such as, e.g., CMP, can be employed if other hard mask materials are employed. The hard mask 18 is removed down to the OPL 16. Then, the OPL 16 can be removed by, e.g., an $O_2$ plasma etch or $N_2/H_2$ plasma etch, etc.

Referring to FIG. 6, after the removal of the OPL 16 and the anneal of the nanorods 26, the nanorods 26 are ready for continued processing. The nanorods 26 can be arranged in any configuration suitable for creating a biosensor and treatment device 10, e.g., an array 52 of electrodes with uniform or non-uniform spacings therebetween. A dielectric film or coating 27 can be deposited over the surface of the nanorods 26 and the metal layer 14 by atomic layer deposition (ALD) or other conformal deposition process to provide electrical insulation when immersed in an aqueous solution or other environment. The coating 27 can include a porous coating that permits electrolytic interaction with an environmental aqueous solution, e.g., to measure pH or other parameter, by permitting interaction of ions with the nanorods 26 through pore or openings. In one embodiment, the coating 27 can include a porous or nonporous silicon oxide, hafnium oxide, aluminum oxide, or other dielectric coating. The coating 27 can be ultra-thin, e.g., less than 2 nm, although thicknesses of up to about 50 nm can be employed.

The coating 27 can be formed, e.g., using ALD, which will be processed to prepare a nanoporous $SiO_2$ film by mixing ALD formed alumina and silica in multiple layers. Each cycle of the ALD process can deposit one of Si or Al with an oxidation after each deposition cycle to form a respective oxide (e.g., $SiO_2$ or $Al_2O_3$). The ALD reagent for forming Al can include $AlMe_3$ while the reagent for forming the $SiO_2$ can include $(Me_2N)_3SiH$ (where Me is a methyl group). The ALD process can include a plurality of cycles to deposit a plurality of layers. The plurality of layers can include a large number (e.g., two to several hundred). The plurality of layers form the coating 27, which includes $SiO_2$ and $Al_2O_3$ having a total thickness of between about 2 nm to about 50 nm. While other dimensions are contemplated, the coating 27 preferably includes a nanoscale thickness.

A wet etch process can be performed on the coating to selectively remove the $Al_2O_3$ from coating 27. The wet chemical etch can include, e.g., etching with phosphoric acid or hydrofluoric acid. The wet etch results in a nanoporous $SiO_2$ layers. This process can be employed with $SiO_2$ alone, $Al_2O_3$ alone or other suitable material.

Openings (not shown) can be formed within the coating 27 to expose an area of each nanorod 26 to permit contact between an aqueous solution surrounding the nanorod 26 and the nanorod 26. Openings can be etched into the coating using an appropriate block mask, lithography or other patterning process.

Referring to FIG. 7, the structure of nanorod array 52 includes chemical sensing electrodes 54 and cell destroying electrodes 56. In a particularly useful embodiment, the nanorods 26 for electrodes 54 and 56 are grouped in an overlapping configuration with pH sensing nanorods intermingled with electrical pulsing electrodes for the treatment of cancer or other diseases. The array 52 can include uniform or non-uniform spacings between electrodes (54, 56); however, non-uniform spacings can be employed. The array 52 can include sensor regions with voltage nano-pulse electrodes 56 adjacent to pH sensing electrodes 54 or the electrodes 54 and 56 can be dual-functional electrodes having pH sensing and high voltage nanopulse capability. The electrodes 54, 56 are computer or circuit controlled.

Cells 60 bound to or in proximity with electrodes 54 (and/or 56) have their pH levels measured to identify regions of cancer cells. Electrodes 54 (and/or 56) can be employed as a pH meter that provides a value as to how acidic or alkaline a liquid is surrounding the electrodes. The concentration of hydrogen ions is measured. Acids dissolve in water forming positively charged hydrogen ions (H+). The greater this concentration of hydrogen ions, the stronger the acid is. Similarly alkali or bases dissolve in water forming negatively charged hydrogen ions (OH−). The stronger a base is the higher the concentration of negatively charged hydrogen ions there are. The amount of these ions present in solution determines the pH. The pH meter includes at least two electrodes (nanorods 26), a reference and a sensor. The pH meter measures essentially the electro-chemical potential of hydrogen ions or the potential of hydrogen.

The electro-chemical potential can be measured through openings in the coating 27 (FIG. 6) or through pores within the coating 27 (FIG. 6).

With an acidic measurement, electric pulses can be generated to destroy the cells or tissue. Studies have demonstrated that the intracellular pH of solid tumors is maintained within a range of 7.0-7.2, whereas the extracellular pH is acidic (less than 7.0). A low extracellular pH may be a factor in determining more aggressive cancer phenotypes. Electrode-measured pH values of human tumors and adjacent normal tissues show that the electrode pH (representing extracellular tissue pH) is substantially and consistently lower in the tumor than in normal tissue. In contrast, intracellular pH is essentially identical or slightly more basic in the tumor as compared to normal tissue. The cellular pH gradient is substantially reduced or reversed in the tumor as compared to normal tissue. In normal tissue, the extracellular pH is relatively basic, and, in tumor tissue, the magnitude of the pH gradient is reduced or reversed. This can be exploited in the treatment of cancer in accordance with aspects of the present invention.

In one embodiment, drugs exhibiting weak acid or basic properties can be introduced to create ionization within cancer tissue. The drug's ionization is strongly dependent on the pH. Weak acidic drugs which are relatively lipid soluble in their non-ionized state may diffuse freely across the cell membrane and, upon entering a relatively basic intracellular compartment, become trapped and accumulate within a cell, leading to substantial differences in the intracellular/extracellular drug distribution between the tumor and normal tissue creating target for cell destruction.

The device 10 can include a battery source or other power source incorporated therein or connected thereto, to serve as the energy source for the electrical nanopulse and sensing functions. Pulses can be applied directly to tissue, creating a transient opening of small pores in cell and organelle membranes. The opening of the pores can be performed in a pulsatile (or on-demand) manner to destroy the cells as needed by applying appropriate voltage or electrical current in specific regions. The nanorods 26 can have a narrow spacing 61 (e.g., between about 20 nm-1000 nm), such that a common voltage applied to the nanorods 26 results in a high electric field intensity between the spacings 61 (or between nanorods of different regions, e.g., between regions 54 and 56). The electric field intensity can be controlled by adjusting voltage (e.g., between about 0.5 volts to about 100 volts (or more)) and current conditions using circuit components or controls integrated into the device 10. In useful embodiments, the nanorods 26 can be subjected to nanosecond (e.g., 0.1 ns to about 500 ns) pulsed electric fields (nsPEF) which can induce apoptosis in cells. Similarly, the nanorods 26 can have a broader spacing 63 (e.g., greater than about 10 nm), such that the common voltage applied to the nanorods 26 for electrodes does not result in a high electric field intensity between the spacings 63 (e.g., to promote growth). The electrodes 54 and 56 can use a same voltage or different voltages to obtain the desired results.

It should be understood that electric field intensity can be adjusted in a plurality of ways. For example, the size, shape and density of the nanorods 26 can be controlled. In other embodiments, pulse shapes (e.g., magnitude, duration, etc. of the voltage) and pulse frequencies can be adjusted and controlled for pulsations of voltage or current to the nanorods. Other electric field intensity controls are also contemplated, e.g., nanorod coatings, etc.

Figure 8:
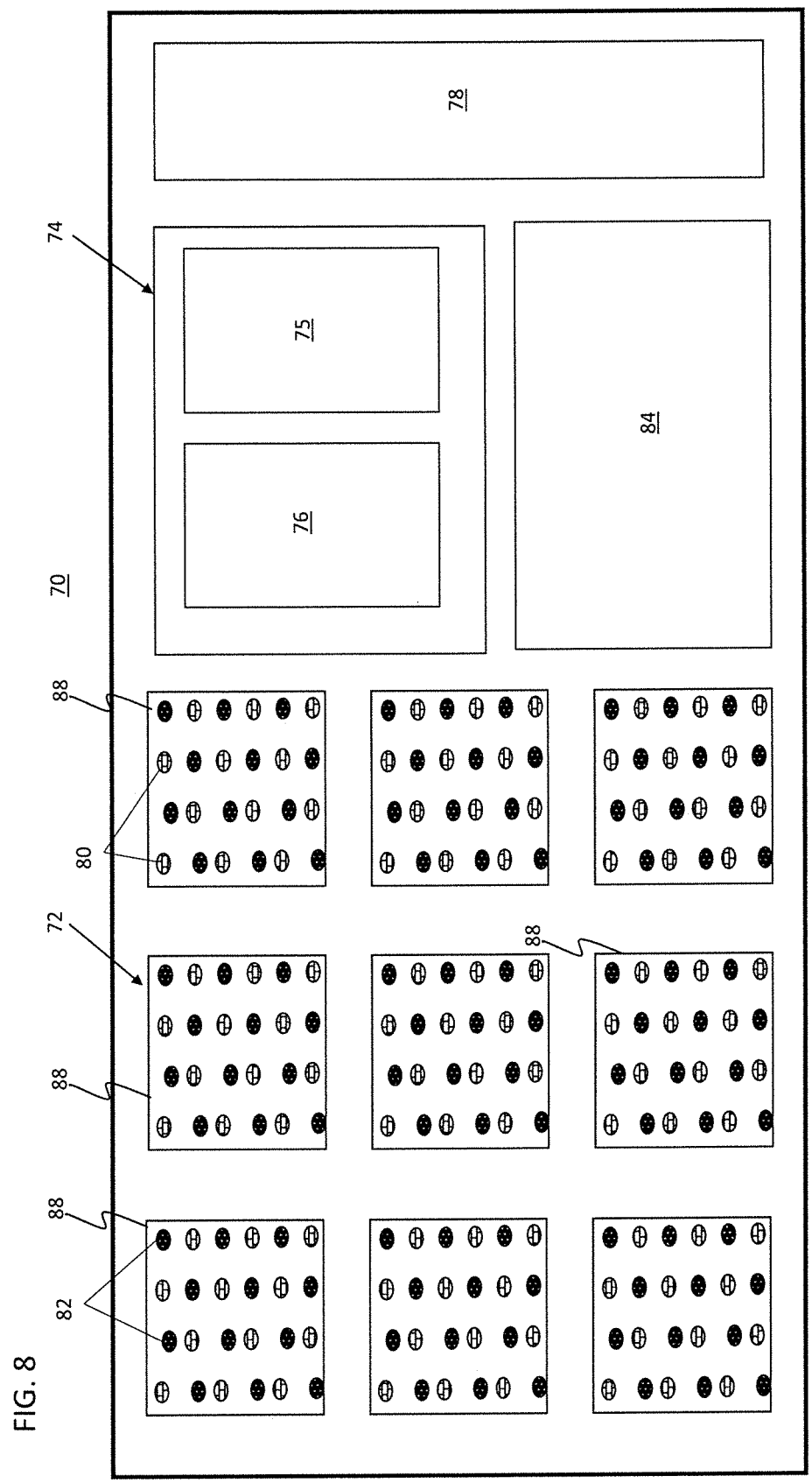
FIG. 8 is a plan schematic view showing a treatment device having nanorods and circuits integrated on a substrate in accordance with an embodiment of the present invention.

Referring to FIG. 8, a device 70 for sensing and treating cancer is illustratively shown in accordance with one embodiment. In one embodiment, the device 70 includes a data processing system 74 that can include data acquisition, storage, processing and communication functions. The device 70 includes an array 72 of electrodes 80 and 82. The array 72 illustratively shows uniform spacings although any spacing configurations can be employed. A circuit or microprocessor of the data processing system 74 can include an array of transistors (e.g., bipolar junction transistors (BJTs)) and/or other circuit components (e.g., integrated into the substrate 12) configured to activate or selectively activate electrodes. The circuits of the data processing system 74 can be integrated into the substrate 12 using semiconductor processing techniques. The circuits of the data processing system 74 can be connected to a high voltage power source, e.g., battery 78, if the device 70 is implantable in the body. Alternatively, the circuit of the data processing system 74 can connect to a separate external power source.

The circuits of the data processing system 74 can be controlled using a controller circuit or microprocessor 76 that generates signals to control which electrodes 80, 82 are activated. The high voltage (e.g., 0.5 to 100 volts) can be programmed to activate the electrodes 80, 82 using a patterned metal layer 14 to connect to the electrodes 80, 82 in localized areas to sense pH or destroy cells using electrical pulses over specific regions of the array 72 or the whole array 72. The activation of the electrodes can selectively kill cells in accordance with measured pH or sensed ionic change in the particular regions. In some embodiments, the nanorod electrodes 80, 82 can produce electrical fields for sensing pH, sensing potential, destroying cancer cells or combinations of these and other tasks. Device 70 can include regions with different spacings between nanorod electrodes 80, 82 in groups or regions 88. In one example, electrodes 80 can include pH sensing electrodes while electrodes 82 can be employed for electrical pulsing. It should be understood that the electrodes 80 or 82 can include dual functionality and are controlled using the microprocessor 76 or circuits formed in the substrate 12. A battery or batteries 78 can be integrated or coupled to the device 70 to provide power to electrodes 80, 82, the data processing system 74 and other components, e.g., a transceiver 84, on the device 70. The data processing system 74 can include the transceiver device 84 (for off or on-chip communications), memory storage 75, microprocessor 76 and other passive or active components (e.g., connections, buffers, gates, etc.).

The device 70 can be made disposable after use. The substrate 12 and other components can be coated or shielded to prevent contamination to the host from materials of the device 70.

Figure 9:
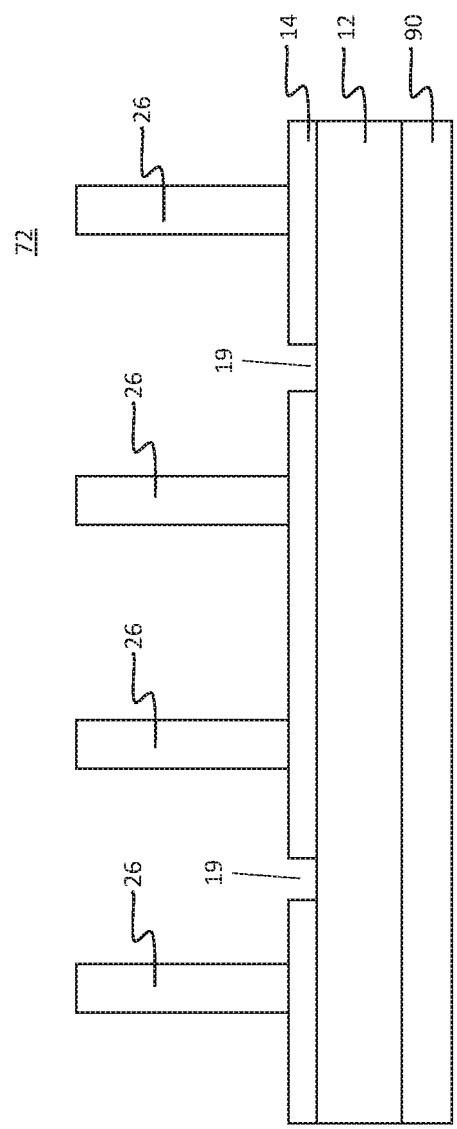
FIG. 9 is a cross-sectional view showing the device of FIG. 6 having a magnetic or magnetically sensitive layer used for guiding the device during deployment in vivo in accordance with an embodiment of the present invention.

Referring to FIG. 9, device or devices 72 can include a magnetically sensitive layer or magnetic layer 90 employed for guiding the device 72. In one embodiment, the devices 72 can be introduced into a body and guided to a location within the body using a magnetic guidance system. The devices 72 are guided in the blood stream or in an open region within the body to a location where treatment is needed. The devices 72 are then positioned to sense and treat a lesion or other tissue. The device 72 can be made disposable after use.

The magnetic layer 90 can include a ferromagnetic material, such as e.g., Fe, Ni, Co, alloys or combinations of these and other suitable magnetic materials. The device 72 with the magnetic layer 90 can be guided and controlled using a coil or coils externally disposed relative to the body.

Figure 10:
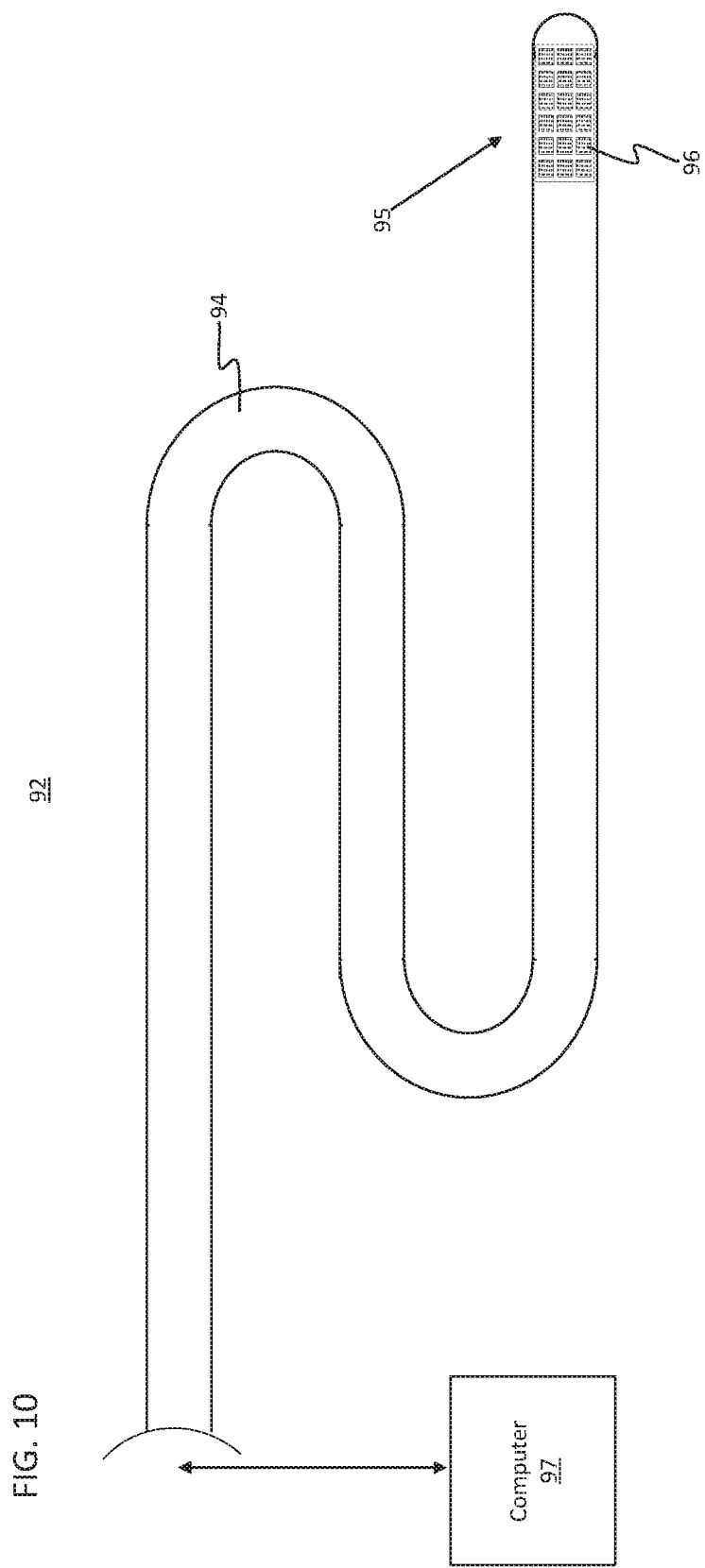
FIG. 10 is a perspective view showing the device mounted on a proximal end portion of an elongated flexible instrument for guiding the device during deployment in vivo in accordance with an embodiment of the present invention.

Referring to FIG. 10, in another embodiment, a flexible elongated instrument or treatment instrument 92 can include a catheter or guidewire 94 having a proximal end portion 95 configured to receive a device 96 (e.g., device 10, 70, 72, etc.) thereon. Since the device 96 can be powered and connected to a computer located remotely (not shown), the device 96 can simply include nanorod electrode arrays for sensing and electrical pulsing functions. In this way, a microprocessor, battery and other components are not needed on the device 96 itself. Alternately, the device 96 can include a computer or workstation 97 and/or other components depicted in FIG. 8 to provide similar functionality as the embodiment described in FIG. 8. The treatment instrument 92 can be introduced into the body, e.g., laparoscopically, and maneuvered to a position adjacent to a region to be treated. The device(s) are then activated for sensing and treating the regions or regions. The device 92 or its proximal tip can be made disposable after use.

Figure 11:
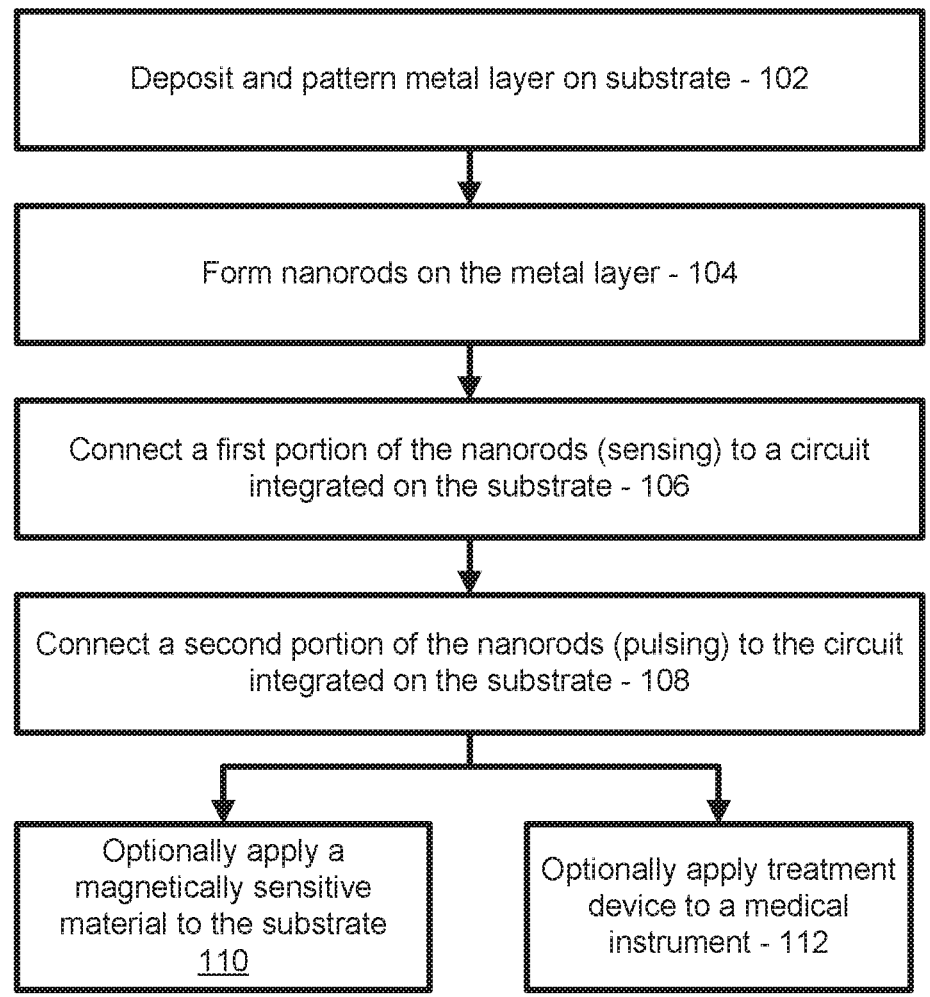
FIG. 11 is a block/flow diagram showing methods for fabricating a treatment device in accordance with embodiments of the present invention.

Referring to FIG. 11, methods for fabricating devices in accordance with the present invention are illustratively shown and described. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 102, a metal layer is deposited and patterned on a substrate. The metal layer patterning can include lithographic patterning to form metal lines to connect to nanorods and groups of nanorods to be formed. It should be understood that a circuit to provide selective activation of the nanorods as electrodes can be performed prior to or concurrently with forming the metal layer and nanorods. The circuit can include an integrated circuit formed within the same substrate as the nanorods are formed on. Alternately, the circuit or chip can connect to or be integrated with the substrate with the nanorods, e.g., an application specific chip can be soldered to the substrate and connected to the nanorods.

The substrate can include a semiconductor material and the processor/data processing system can be formed in the substrate by semiconductor processing. The processor controls activation of the nanorods. Metal paths can be formed by patterning the metal layer on which the nanorods are formed to create such connections. The metal paths and other components (e.g., transistors (e.g., BJTs), logic gates, etc.) can form pulse circuits. The pulse circuits can be formed on or in the substrate and employed to generate signals for rapid pulses of energy (e.g., nsPEF). By controlling how often the rapid pulses of energy are sent out (pulse timing), and their magnitude, cell destruction or stimulation actions can be achieved.

In block 104, nanorods are formed on the metal layer. This includes the formation of a mask or masking and etching a resist or OPL through the mask to provide openings where nanorods are formed. A plating or other deposition process can be employed to fill the openings down to the metal layer. The mask and resist (or OPL) are then removed to expose the nanorods.

In block 106, first portions of the nanorods are connected to an integrated processor (e.g., microprocessor or controller) to function as sensor electrodes. This can include connecting the processor to the metal layer or portions of the metal layer. In one embodiment, transistors can be employed to selectively connect the nanorods to the processor.

In block 108, second portions of the nanorods are connected to the integrated processor to function as electrical pulsing electrodes. This step can be performed concurrently or sequentially with block 106. Connecting second portions can include connecting the processor to the metal layer or portions of the metal layer. In one embodiment, transistors can be employed to selectively connect the nanorods to the processor. The transistors can be selectively switched so that the first and second electrodes can include dual functionality and perform either of sensing and/or electrical pulsation. In one example, the sensing (e.g., pH sensing) identifies cancer cells and the electrical pulsation kills the cancer cells for treating cancer with the medical treatment device.

In block 110, a magnetic or magnetically sensitive layer may optionally be formed on the substrate. The magnetic layer can be employed in a guidance embodiment, where the magnetic layer responds to a magnetic coil or coils (e.g., external or internal to the body) to direct the device (e.g., medical treatment device) with the magnetic layer to a treatment location within the body.

In block 112, in another embodiment, the medical treatment device can be mounted on a flexible elongated medical instrument (e.g., a catheter or guidewire) for deployment in vivo. The medical treatment device can then be laparoscopically deployed in vivo on a proximal end of the flexible elongated medical instrument.

Figure 12:
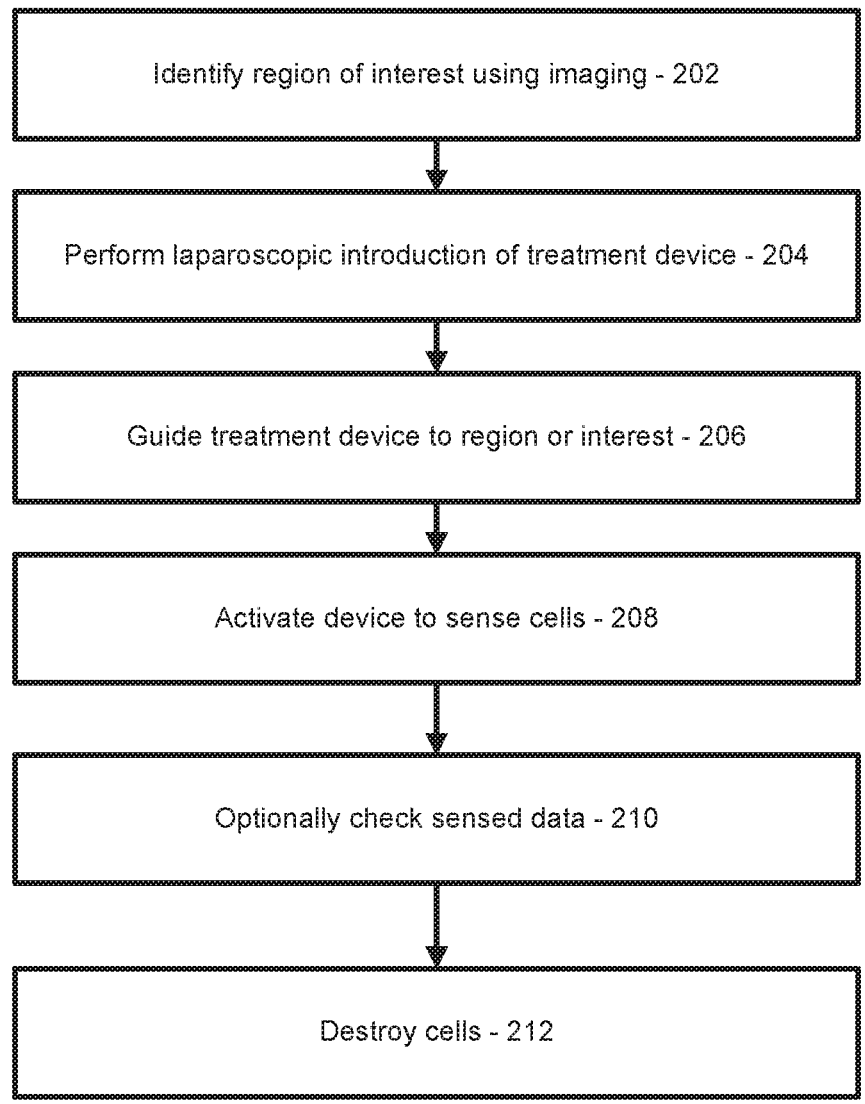
FIG. 12 is a block/flow diagram showing methods for deploying the treatment device in accordance with embodiments of the present invention.

Referring to FIG. 12, methods for employing the medical treatment device for the treatment of cancer or other applications is illustratively shown. In block 202, a region of interest is identified using an imaging technique. The imaging technique can include, fluoroscopy, computed tomography, magnetic resonance imaging, ultrasound or any other suitable imaging technique.

In block 204, laparoscopic surgery can be performed to introduce a flexible elongated instrument or to inject the medical treatment device or devices into the body. In block 206, the medical treatment device is guided to the region of interest (e.g., using an instrument, using magnetic guidance coils, employing other guidance devices, etc.). Target positions can be programmed into the devices and guided to the positions where a signal will indicate a designated location has been achieved. When the location is reached and maintained, the functions of the device can be activated. In block 208, the medical treatment device is activated to sense. Sensors on the medical treatment device sense the location of cancer cells or other cells.

In block 210, a medical professional can optionally check the sensor data to ensure probes or sensors are correctly aligned and in contact with cancer cells. Optionally a camera can be employed with the medical treatment device (e.g., a scope or the like) to validate the position of the voltage delivering electrodes on the medical treatment device. Targeted positions can also be verified digitally using a positioning system and the programmed locations in the devices.

In block 212, voltage or current is delivered to destroy the targeted cells in accordance with the sensed data. The voltage or current can be pulsed. The treatment continues using the appropriate feedback to ensure the destruction of all the cancer cells without damage to healthy tissues.

Having described preferred embodiments for intelligent and disposable devices for selective electrical stimulation of apoptosis (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A treatment device, comprising:
   an array of metal nanorod electrodes formed on a substrate, the array including first electrodes for sensing, and second electrodes for generating an electrical pulsation from energy received from a power source; and
   a data processing system including circuitry configured to monitor a parameter that indicates a condition using the first electrodes, and the circuitry configured to activate the electrical pulsation in the second electrodes in accordance with a reading of the parameter, the circuitry conditioning energy received from a power source such that the generated electrical pulsation induces apoptosis in cells in accordance with the condition.

2. The device as recited in claim 1, wherein the first and second electrodes are configured to have dual functionality with respect to sensing and electrical pulsation.

3. The device as recited in claim 1, wherein the substrate includes a semiconductor material and the circuitry is formed in the substrate.

4. The device as recited in claim 1, wherein the parameter includes pH measured to identify cancer cells and the electrical pulsation is employed to kill the cancer cells.

5. The device as recited in claim 1, further comprising a magnetically sensitive layer formed on the substrate, the magnetically sensitive layer being configured to guide the device to a treatment location.

6. The device as recited in claim 5, wherein the device is further configured to be guided and controlled by at least one magnetic coil external to a body using the magnetically sensitive layer formed on the substrate and deployed in vivo.

7. The device as recited in claim 1, wherein the data processing system includes data acquisition, storage, processing and communication functions.

8. A treatment device, comprising:
- a flexible elongated instrument configured for deployment in vivo;
- an array of metal nanorod electrodes formed on a substrate and mounted on a proximal end portion of the flexible elongated instrument, the array including first electrodes for pH sensing, and second electrodes for generating an electrical pulsation from energy received from a power source; and
- a data processing system including circuitry configured to monitor pH using the first electrodes, and the circuitry configured to activate the electrical pulsation in the second electrodes in accordance with a pH reading, the circuitry conditioning energy received from a power source such that the generated electrical pulsation induces apoptosis in cells in accordance with the pH reading.

9. The device as recited in claim 8, wherein the first and second electrodes include dual functionality and perform either of pH sensing and electrical pulsation.

10. The device as recited in claim 8, wherein the substrate includes a semiconductor material and the circuitry is formed in the substrate.

11. The device as recited in claim 8, wherein the pH sensing identifies cancer cells and the electrical pulsation kills the cancer cells.

12. The device as recited in claim 8, wherein the flexible elongated instrument includes connectors configured to connect the array remotely to a computer associated with the data processing system that controls the nanorod electrodes.

* * * * *